United States Patent [19]

Young et al.

[11] Patent Number: 4,962,117
[45] Date of Patent: Oct. 9, 1990

[54] HETERAZOLE DIALKANOIC ACIDS

[75] Inventors: Robert N. Young, Senneville; Joseph G. Atkinson, Montreal, both of Canada

[73] Assignee: Merck Frosst Canada, Inc., Kirkland, Canada

[21] Appl. No.: 265,972

[22] Filed: Nov. 2, 1988

Related U.S. Application Data

[63] Continuation-in-part of Ser. No. 125,622, Nov. 25, 1987, abandoned.

[51] Int. Cl.5 .................. C07D 277/30; C07D 263/32; C07D 233/26; A61K 31/425
[52] U.S. Cl. .................... 514/365; 514/340; 514/341; 514/342; 514/369; 514/370; 514/371; 514/374; 514/376; 514/377; 514/182; 514/392; 514/398; 514/400; 546/275; 546/278; 546/280; 548/187; 548/194; 548/195; 548/200; 548/201; 548/204; 548/229; 548/233; 548/236; 548/252; 548/315; 548/337; 548/342
[58] Field of Search ............... 548/204, 236, 342, 252, 548/229, 195, 233, 337, 315, 187, 194, 200, 201; 546/278, 275, 280; 514/365, 369, 370, 371, 346, 341, 342, 374, 376, 377, 392, 398, 400

[56] References Cited

U.S. PATENT DOCUMENTS 4,826,990 5/1989 Musser .................. 548/203

FOREIGN PATENT DOCUMENTS 219436 4/1987 European Pat. Off. ............ 548/204
228959 7/1987 European Pat. Off. ............ 548/204

*Primary Examiner*—Robert Gerstl
*Attorney, Agent, or Firm*—Gabriel Lopez; Hesna J. Pfeiffer

[57] ABSTRACT

Compounds having the formula:

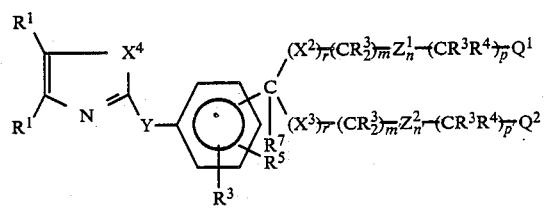

are leukotriene antagonists and inhibitors of leukotriene biosynthesis. These compounds are useful as antiasthmatic, antiallergic, anti-inflammatory, and cytoprotective agents.

12 Claims, No Drawings

HETERAZOLE DIALKANOIC ACIDS

CROSS-REFERENCE

This is a CIP of U.S. Ser .No. 125,622, filed Nov. 25, 1987 now abandoned.

BACKGROUND OF THE INVENTION

The leukotrienes and their biological activities, especially their roles in various disease states and conditions have been described. For example, see U.S. Pat. No. 4,683,325 (July 28, 1987), which is incorporated herein by reference.

Several classes of compounds exhibit the ability to antagonize the action of leukotrienes in mammals, especially humans. See for example: U.K. Pat. No.2,058,785 and 2,094,301; and EP 56,172, 61,800 and 68,739.

EP 110,405 (June 13, 1984) describes anti-inflammatory and antiallergic substituted benzenes which are disclosed to be leukotriene inhibitors, i.e., inhibitors of the 5-lipoxygenase pathway.

SUMMARY OF THE INVENTION

The present invention relates to compounds having activity as leukotriene and SRS-A antagonists or inhibitors of the biosynthesis of the leukotrienes, to methods for their preparation, to intermediates useful in their preparation and to methods and pharmaceutical formulations for using these compounds in mammals (especially humans).

Because of their activity as leukotriene antagonists or biosynthetic inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemic; noxious agent induced damage or necrosis of hepatic, pancreatic, renal, or myocardial tissue: liver parenchymal damage caused by hepatoxic agents such as CCl4 and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compounds of this invention are best realized by Formula I:

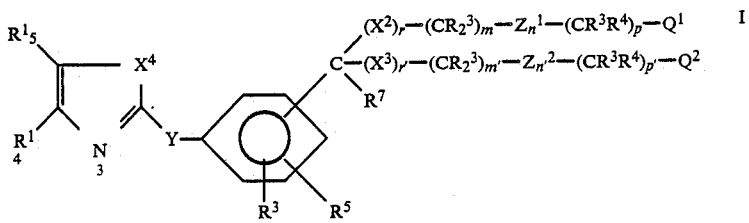

wherein:
$R^1$ is H, halogen, $C_1$—$C_8$ alkyl, $C_2$—$C_8$ alkenyl, $C_2$—$C_8$ alkynyl, —$CF_3$, —$SR^2$, —$S(O)R^2$, —$S(O)_2R^2$, —$NR^3R^3$, —$OR^3$, —$COOR^3$ —(C=O)$R^3R^3$, —CN, —$NO_2$, —$N^3$ substituted or unsubstituted phenyl, substituted or unsubstituted benzyl, substituted or unsubstituted 2-phenethyl, or substituted or unsubstituted pyridyl;

$R^2$ is $C_1$—$C_8$ alkenyl, $C_2$—$C_8$ alkynyl, —$CF_3$, substituted or unsubstituted phenyl, substituted or unsubstituted benzyl, or substituted or unsubstituted 2-phenethyl;

$R^3$ is H or $R^2$;

$R^4$ is H, halogen, —$NO_2$, —CN, —$OR^3$, —$SR^3$, $NR^3R^3$, or $C_1$—$C_8$ alkyl;

$CR^3R^4$ may be the radical of a naturally occurring amino acid;

$R^5$ is H, halogen, —$NO_2$, —$N_3$, —CN, —$SR^2$, —$NR^3R^3$, —$OR^3$, $C_1$—$C_8$ alkyl, or —(C=O)$R^3$;

$R^6$ is —(CH$_2$)$_s$—C($R^7R^7$)—(CH$_2$)$_s$—$R^8$ or —CH$_2$CONR$^{12}R^{12}$;

$R^7$ is H or $C_1$—$C_4$ alkyl;

$R^8$ is (A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or (B) the radical W-$R^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is —$SR^{11}$, —$OR^{12}$, or —$NR^{12}R^{12}$;

$R^{11}$ is $C_1$—$C_6$ alkyl, unsubstituted phenyl, or unsubstituted benzyl;

$R^{12}$ is H, $R^{11}$, or two $R^{12}$ groups joined to the same N may form a ring of 5 or 6 members containing up to two heteroatoms chosen from O, S or N;

$R^{13}$ is $C_1$—$C_8$ alkyl, $C_2$—$C_8$ alkenyl, $C_2$—$C_8$ alkynyl, —$CF_3$, or unsubstituted phenyl, benzyl, or 2-phenethyl;

$R^{14}$ is H or $R^{13}$;

$R^{15}$ is $R^3$ or halogen;

$R^{16}$ is H, $C_1$—$C_4$ alkyl, or OH;

m and m' are independently 0-8;

n and n' are independently 0 or 1;

p and p' are independently 0-8;

m+n+p is 1-10 when $X^2$ is O, S, S(O), or S(O)$_2$;

m+n+p is 0-10 when $X^2$ is $CR^3R^{16}$;

m'+n'+p' is 1-10 when $X^3$ is O, S, S(O), or S(O)$_2$;

m'+n'+p' is 0-10 when $X^3$ is $CR^3R^{16}$;

r is 0 or 1 when $Z^1$ is HET (—$R^3$, —$R^5$);

r is 1 when $Z^1$ *is* —*CONR3*;

r' is 0 or 1 when $Z^2$ is HET($-R^3$, $-R^5$);
r' is 1 when $Z^2$ is $CONR^3$;
s is 0–3;
$Q^1$ and $Q^2$ are independently $-COOR^3$, tetrazole, $-COOR^6$, $-CONHS(O)_2R^{13}$, $-CN$, $-CONR^{12}R^{12}$, $-CHO$, $-CH_2OH$, $-COCH_2OH$, $-NHS(O)_2R^{13}$; or if $Q^1$ or $Q^2$ is COOH and $R^4$ is $-OH$, $-SH$, or $-NHR^3$ then $Q^1$ or $Q^2$ and $R^4$ and the carbons through which they are attached may form a heterocyclic ring by loss of water;
W is O, S, or $NR^3$;
$X^1$ is O, S, $-S(O)-$, $-S(O)_2-$, $-NR^3$, or $-CR^3R^3-$
$X^2$ and $X^3$ are independently O, S, S(O), $S(O)_2$, or $CR^3R^{16}$;
$X^4$ is $NR^3$, O, or S;
Y is $-CR^3=CR^3-$, $-C\equiv C-$, $-CR^3R^3-X^1-$, $-X^1-CR^3R^3-$, $-CR^3R^3-X^1-CR^3R^3-$,

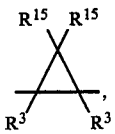

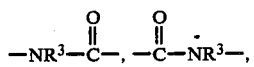

C=O,
O, S, or $NR^3$;
$Z^1$ and $Z^2$ are independently $-CONR^3-$ or $-HET(-R^3,-R^5)-$;
HET is

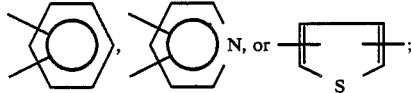

and the pharmaceutically acceptable salts thereof.

Alkyl, alkenyl and alkynyl are intended to include linear, branched, and cyclic structures and combinations thereof.

As used herein, the term "alkyl" includes "loweralkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-ethyl-2,2-methyl-4-propylnonyl, cyclododecyl, adamantyl, and the like.

As used herein, the term "loweralkyl" includes those alkyl groups of from 1 to 7 carbon atoms. Examples of loweralkyl groups include methyl, ethyl, propyl, isopropyl, butyl, sec- and tert-butyl, pentyl, hexyl, heptyl, cyclopropyl. cyclobutyl, cyclopentyl, cyclohexyl, cycloheptyl, 2-methyl-cyclopropyl, cyclopropylmethyl, and the like.

Alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

As used herein, the term "alkoxy" includes those alkoxy groups of from 1 to 3 carbon atoms of either a straight, branched, or cyclic configuration. Examples of alkoxy groups include methoxy, ethoxy, propoxy, isopropoxy, cyclopropyloxy, and the like.

Substituted phenyl, benzyl, and 2-phenethyl, and pyridyl include 1 or 2 substituents on the aromatic ring selected from $C_1-C_6$ alkyl, $R^{10}$, $NO_2$, $SCF_3$, $-COR^7$, $-COR^{10}$, CN, halogen, and $CF_3$.

Halogen includes F, Cl, Br and I. The prodrug esters of Q (i.e., when Q=$-COOR^6$) are intended to include the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3, 451–454 (1987).

When Q and $R^4$ and the carbons through which they are attached form a ring, the rings thus formed include lactones, lactams, and thiolactones.

It is intended that the definitions of any substituent (e.g., $R^1$, $R^2$, m, Q, X, etc.) in a particular molecule be independent of its definitions elsewhere in the molecule. Thus, $-NR^3R^3$ represents $-NHH$, $-NHCH_3$, $-NHC_6H_5$, etc.

The heterocycles formed when two $R^{12}$ groups join through N include pyrrolidine, piperidine, morpholine, thiamorpholine, piperazine, and N-methylpiperazine.

The naturally occurring amino acids, the radicals of which may be $CR^3R^4$, include alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine.

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Preferred compounds of Formula I are those wherein:
$R^1$ is H, halogen, $C_1-C_8$ alkyl, $-CF_3$, $-SR^2$, $-S(O)R^2$, $-S(O)_2R^2$, $-OR^3$, or $-CN$;
$R^2$ is $C_1-C_8$ alkyl or $-CF_3$;
$R_3$ is H or $R^2$;
$R_4$ is H, $-OR^3$, $-SR^3$, $NR^3R^3$, or $C_1-C_8$ alkyl;
$CR^3R^4$ may be the radical of a naturally occurring amino acid;
$R^5$ is H, halogen, $-CN$, $-SR^2$, $-OR^3$, $C_1-C_8$ alkyl, or $-(C=O)R^3$;
$R^6$ is $-(CH_2)_s$, $-C(R^7R^7)-(CH_2)_s-R^8$ or $-CH_2CONR^{12}R^{12}$;
$R^7$ is H or $C_1-C_4$ alkyl;
$R^8$ is (A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or (B) the radical $W-R^9$;
$R^9$ contains up to 21 carbon atoms and is (1) a hydrocarbon radical or (2) an acyl radical of an organic acyclic or monocyclic carboxylic acid containing not more than 1 heteroatom in the ring;
$R^{10}$ is $-SR^{11}$, $-OR^{12}$, or $-NR^{12}R^{12}$;
$R^{11}$ is $C_1-C_6$ alkyl, $-(C=O)R^{14}$, unsubstituted phenyl, or unsubstituted benzyl;
$R^{12}$ is H, $R^{11}$, or two $R^{12}$ groups joined to the same N may form a ring of 5 or 6 members containing up to two heteroatoms chosen from O, S or N;

$R^{13}$ is $C_1$—$C_8$ alkyl, —$CF_3$, or unsubstituted phenyl, benzyl, or 2-phenethyl;
$R^{14}$ is H or $R^{13}$;
$R^{15}$ is $R^3$ or halogen;
$R^{16}$ is H, $C_1$—$C_4$ alkyl, or OH;
m and m' are independently 0–4;
n and n' are independently 0 or 1;
p and p' are independently 0–4;
m+n+p is 1–10 when $X^2$ is O or S;
m+n+p is 0–10 when $X^2$ is $CR^3R^{16}$;
m'+n'+p' is 1–10 when $X^3$ is O or S;
m'+n'+p' is 0–10 when $X^3$ is $CR^3R^{16}$;
r is 0 or 1 when $Z^1$ is HET (—$R^3$, —$R^5$);
r is 1 when $Z^1$ is —$CONR^3$;
r' is 0 or 1 when $Z^2$ is HET(—$R^3$, —$R^5$);
r' is 1 when $Z^2$ is $CONR^3$;
s is 0–3;
$Q^1$ and $Q^2$ are independently —$COOR^3$, tetrazole, —$COOR^6$, —$CONHS(O)_2R^{13}$, —$CONR^{12}R^{12}$, —$NHS(O)_2R^{13}$; or if $Q^1$ or $Q^2$ is COOH and $R^4$ is —OH, —SH, or —$NHR^3$ then $Q^1$ or $Q^2$ and $R^4$ and the carbons through which they are attached may form a heterocylic ring by loss of water;
W is O, S, or NH;
$X^1$ is O, S, —$NR^3$, or —$CR^3R^3$—;
$X^2$ and $X^3$ are independently O, S, or $CR^3R^{16}$;
$X^4$ is $NR^3$, O, or S;
Y is —$CR^3=CR^3$—, —$C\equiv C$—, —$CR^3R^3$—$X^1$—, or —$X^1$—$CR^3R^3$—;
$Z_1$ and $Z^2$ are independently —$CONR^3$—or —HET-(—$R^3$, —$R^5$)—;
HET is

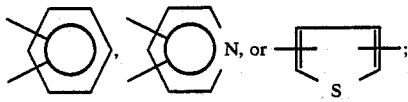

and the pharmaceutically acceptable salts thereof.

It will be understood that in the discussion of methods of treatment which follows, references to the compounds of Formula I are meant to also include the pharmaceutically acceptable salts and the lactone, lactam, and thiolactone forms.

The compounds of Formula I are active as antagonists of SRS-A and especially of leukotriene $D_4$. These compounds also have modest inhibitory activity on leukotriene biosynthesis but are primarily of therapeutic interest as antagonists. The activity of the compounds of Formula I can be detected and evaluated by methods known in the art. See for example, Kadin, U.S. Pat. No. 4,296,129.

The ability of the compounds of Formula I to antagonize the effects of the leukotrienes and to inhibit the biosynthesis of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. They are also effective in the treatment of inflammatory diseases of the eye.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are: (A) an ethanol-induced lesion assay and (B) an indomethacin-induced ulcer assay and are described in U.S. Pat. No.4,683,325 (July 28, 1987).

The leukotriene antagonist properties of compounds of the present invention are evaluated using the following assays.

Guinea-Pig Ileum Preparation for Evaluation of Antaqonists of Leukotriene $D_4$ and Other Mediators Tissue:

Sections of ileum are taken from male Hartley strain guinea pigs (Charles River, U.S.A.) 300 to 500 g which were sacrificed by a blow to the head and exsanguinated. Terminal ileum is removed, cleaned with warm Tyrode's solution and then divided into segments of approximately 1.5–2.0cm each. The segments of ileum are then mounted under 1 g tension in a 20 ml organ bath containing 10 ml of Tyrode's solution with the following composition (mM): NaCl, 137; KCl, 2.7; $MgSO_4.7H_2O$, 0.8; $CaCl_2$, 1.8; $NaH_2PO_4$, 0.42; $NaHCO_3$, 11.9; Dextrose, 5.6. The bathing solution is continuously aerated with $95O_2$ and 5% $CO_2$ and bath temperature is maintained at 37° C. The beta-adrenoceptor blocker, timolol (0.5 μg/ml) and the antimuscarinic agent atropine (1.0 μM) are present in the Tyrode's solution. Isometric tension changes are recorded using Grass FT03 force displacement transducers (Grass Instrument G., Quincy, Mass.) connected to a Beckman Type R Dynograph. The output (analog) signals from all channels of the Beckman Dynograph are converted to digital signals (DL-12 Data Logger, Buxco Electronics). These signals are subsequently fed into an IBM-XT computer for storage and subsequent analysis (Buxco Electronics Custom Software). In order to wash tissue, the bath solution is automatically aspirated and replaced with a constant volume (10 ml) of fresh solution by means of timer controlled solenoid valves. Antagonist Testing:

After the tissues are stable, a standard dose of 0.3 ng/ml $LTD_4$ (100 μl) is repeatedly added (timer controlled Harvard Pump) to the bath every 4.5 minutes (1 minute contact, 30 second wash, 3 minute rest) until a consistent response is obtained (minimum of 4 responses). Addition of $LTD_4$ is performed automatically with two 4-channel Harvard Apparatus Syringe Pumps which deliver 100 μl (final bath concentration 0.3 ng/ml) of agonist simultaneously to all tissues every 4.5 minutes. Following each addition of $LTD_4$ the tissue is washed with Tyrode's solution until baseline tension is re-established. After consistent responses are obtained the tissues are used to screen compounds.

Usually, 10 μl of a 10 mg/ml solution of the compound to be tested is added to the bath 30 seconds prior tot he addition of $LTD_4$. The compound and $LTD_4$ remain in contact with the tissue until the maximum tension is developed (1 minute) after which the tissue is washed repeatedly until the baseline is re established. Percent inhibition relative to the immediately preceding control response is computed on an IBM XT for each dose of test compound (Buxco Electronics Custom Software). If the compound is active (greater than 50% inhibition) then tests are performed with 10 fold serial dilutions until inhibition is less than 50%. Provided the response is inhibited by less than 20%, the tissue is used immediately to evaluate another compound. When the response is inhibited by greater than 20%, cycles of LTD4 alone are added until a consistent response is re-established.

In order to determine the specificity of the active compounds, they are tested against contractions induced by a standard dose of histamine (50 ng/ml) using a similar protocol to that described above (½ minute contact time, 30 seconds wash and 2 minutes rest).

LTD$_4$ Binding:

The results for LTD$_4$ binding are determined by the method of S.S. Pong and R.N DeHaven, Proc. Nat. Acad. Sci. USA, 80, 7415-7419 (1983).

Compounds of Formula I are tested using the following assay to determine their mammalian leukotriene biosynthesis inhibiting activity.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/ml. A 500 μl aliquot of PMN suspension and test compound are preincubated for 2 minutes at 37° C., followed by the addition of 10 μM A-23187. The suspension is stirred for an additional 4 minutes then bioassayed for LTB$_4$ content by adding an lliquot to a second 500 μl portion of the PMN at 37° C. The LTB$_4$ produced in the first incubation causes aggregation of the second PMN, which is measured as a change in light transmission. The size of the assay aliquot is chosen to give a submaximal transmission change (usually $-70\%$) for the untreated control. The percentage inhibition of LTB$_4$ formation is calculated from the ratio of transmission change in the sample to the transmission change in the compound-free control.

The following assays can be used to evaluate compounds which are either leukotriene antagonists or inhibitors of leukotriene biosynthesis, or which possess a combination of these two properties.

Antigen Challenge 'in vitro' Assay

Male guinea pigs weighing 300-350 g are sensitized by injecting (intraperitoneally) 0.5 ml of a suspension containing 0.4 mg of egg albumin (Ovalbumin, Grade V, Sigma Chemical Co.) and 4.0 g aluminum hydroxide in 19.6 ml of saline. Two weeks are permitted for sensitization to occur.

Three sensitized guinea pigs are stunned and exanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No.7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine ($7\times10^{-6}$M), atropine ($1 \times10^{-7}$M), and indomethacin ($1.4\times10^{-6}$M) are added to the buffer to block the response to released histamine, acetylcholine, and cyclooxygenase products. To record responses; one end of the tracheal chain is attached to a Gould-Statham UC-2 force displacement transducer which is connected to a Beckman Type R-dynograph. The preparations are allowed to equilibrate for one hour during which time the tissues are automatically washed (10 ml volume displacement) every 6 minutes.

[1] modified Krebs solution in grams/liter and (mM): NaCl - 6.87 (120); glucose - 2.1 (11); NaHCO$_3$ -2.1 (25); KCl - 0.32 (4.72); CaCl$_2$ - 0.28 (2.5); MgSO$_4$.7H$_2$O - 0.11 (0.5); KH$_2$PO$_4$ - 0.16 (1.2); pH at bathing solution=7.35±0.05.

After the equilibration period the tissues are primed with methacholine (10 μg/ml), washed, and allowed to recover to baseline. The tissues are treated again with a second dose of methacholine, washed, allowed to return to baseline and washed for an additional hour.

Two chains are used as a control. These are incubated in a concentration of egg albumin sufficient to induce an average contraction of 50-80% of the methacholine response.

Each compound to be tested is added (at a final bath concentration of 10 μg/ml) 20 minutes prior to challenging the tissue with egg albumin.

The response of the challenged tissue is expressed as a percentage of the methacholine maximum. The percentage inhibition for each compound is then calculated. Compounds which at 10 μg/ml (final concentration) inhibit the egg albumin response by 50% or more are retested at a lower concentration.

Asthmatic Rat Assay

Rats are obtained from an inbred line of asthmatic rats. Both female (190-250 g) and male (260 to 400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one and of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. They are used between days 12 and 14 postsensitization. In order to eliminate the serotonin component of the response, rats are pretreated intravenously 5 minutes prior to aerosol challenge with 3.0 µg/kg of methysergide. Rats are then exposed to an aerosol of 3% EA in saline for exactly 1 minute, then their respiratory profiles are recorded for a further 30minutes. The duration of continuous dyspnea is measured from the respiratory recordings.

Compounds are generally administered either orally 1–4 hours prior to challenge or intravenously 2 minutes prior to challenge. They are either dissolved in saline or 1g methocel or suspended in 1g methocel. The volume injected is 1 ml/kg (intravenously) or 10 ml/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal antiinflammatory drug (NSAID) that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans will generally range from about 0.1 mg/kg to about 100 mg/kg, preferably from about 1 mg/kg to about 100 mg/kg. The dosage may be administered in single or divided individual doses The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts derived from inorganic bases include aluminum, ammonium, calcium, copper, ferric, ferrous, lithium, magnesium, manganic, manganous, potassium, sodium, zinc salts and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethel morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric and p-toluenesulfonic acid, and the like. Particularly preferred are hydrobromic, hydrochloric, phosphoric, and sulfuric acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

Dosage forms include tablets, troches, dispersions, suspensions, solutions, capsules, creams, ointments, aerosols, and the like.

For use where a composition for intravenous administration is employed, a suitable dosage range for anti-asthmatic, anti-inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser, or as a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of Compound I include transdermal devices, aerosols, creams, ointments, lotions, dusting powders, and the like.

For the treatment of diseases of the eye, ophthalmic preparations for ocular administration comprising 0.001-1% by weight solutions or suspensions of the compounds of Formula I in an acceptable ophthalmic formulation may be used.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered be controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |
| Tablet | mg/tablet |
| Compound of Formula I | 25 |
| Microcrystalline Cellulose | 415 |
| Providone | 14.0 |
| Preelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof. NSAIDs which are within the scope of this invention are those disclosed in U.S. Pat. No. 4,683,325 (July 28, 1987).

Pharmaceutical compositions comprising the Formula I compounds may also contain inhibitors of the biosynthesis of the leukotrienes such as are disclosed in U.S. Pat. No.4,666,907 (Apr. 19, 1987), U.S. Pat. No. 4,663,307 (May 5, 1987), U.S. Pat. No. 4,611,056 (Sept. 9, 1986), and U.S. Pat. No. 4,634,766 (Jan. 6, 1987), which are hereby incorporated herein by reference.

The compounds of the Formula I may also be used in combination with leukotriene antaqonists such as those disclosed in EP 106,565 (Apr. 25, 1984) and EP 104,885 (Apr. 4, 1984) which are hereby incorporated herein by reference and others known in the art such as those disclosed in EP 56,172 (July 21, 1982) and U.S. Pat. No. 4,424,231 (Jan. 3, 1984); and in U.K. Pat. Specification No. 2,058,785, which are hereby incorporated herein by reference.

Pharmaceutical compositions comprising the Formula I compounds may also contain as the second active ingredient prostaglandin including thromboxane antagonists such as those disclosed in U.S. Pat. No. 4,536,507 (Aug. 20, 1985), U.S. Pat. No. 4,237,160 (Dec. 2, 1980), EP 166,591 (Jan. 2, 1986), and EP 234,708 (Sept. 2, 1987). They may also contain histidine decarboxylase inhibitors such as α-fluoro-methyl-histidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ATPase inhibitor such as omeprazole, disclosed in U.S. Pat. No. 4,255,431, and the like. Another useful pharmaceutical composition comprises the Formula I compounds in combination with serotonin antagonists such as methysergide, the serotonin antagonists disclosed in *Nature*, vol. 316, pages 126-131, 1985, and the like. Each of the references referred to in this paragraph is hereby incorporated herein by reference.

When the second active ingredient in compositions of this invention is a thromboxane synthetase inhibitor, such inhibitor can be as described in UK Pat. No. 2,038,821 (e.g., UK-37248 and dazoxiben hydrochloride), U.S. Pat. No. 4,217,357 (e.g., UK-34787), U.S. Pat. No. 4,444,775 (e.g., CGS 13080), U.S. Pat. No. 4,226,878 (e.g., ONO 046), U.S. Pat. No. 4,495,357 (e.g., U63557A), U.S. Pat. No. 4,273,782 (e.g., UK-38485), or EP 98,690 (e.g., CV-4151).

The combination compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration. These compositions are formulated similarly to the compositions discussed above.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following compounds (formula I') are within the scope of the invention:

TABLE 1

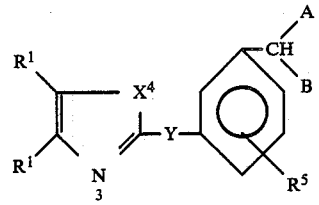

| EXAM. | $R^1, R^1$ | $X^4$ | Y | $R^5$ | A | B |
|---|---|---|---|---|---|---|
| 1 | H, H | S | CH=CH | H | $SCH_2CH_2CO_2H$ | $SCH_2CH_2CO_2H$ |
| 2 | H, 4-CH(CH$_3$)$_2$ | S | CH=CH | H | $SCH_2CH_2CO_2H$ | $SCH_2CH_2CO_2H$ |
| 3 | H, 5-CH(CH$_3$)$_2$ | S | CH=CH | H | $SCH_2CH_2CO_2H$ | $SCH_2CH_2CO_2H$ |
| 4 | H, 4-CH(CH$_3$)$_2$ | O | CH=CH | 6-CH$_3$ | $SCH_2CH_2CO_2H$ | $SCH_2CH_2C(O)N(CH_3)_2$ |
| 5 | H, 4-CH(CH$_3$)$_2$ | NCH$_3$ | CH=CH | H | $SCH_2CH_2CO_2H$ | $SCH_2CH_2CO_2H$ |
| 6 | CH$_3$, CH$_3$ | S | CH$_2$O | 4-Br | $SCH_2CH_2CO_2H$ | 3-(CO$_2$H)Phe |
| 7 | H, Cl | S | CH$_2$S | H | $SCH_2CH_2C(O)N(CH_3)_2$ | CH$_2$CH$_2$—2-(CO$_2$H)Phe |
| 8 | H, 5-CF$_3$ | S | CH=CH | H | $SCH_2CH_2CO_2H$ | 2-(CO$_2$H)—Phe |
| 9 | H, 4-CH(CH$_3$)$_2$ | S | C≡C | H | $SCH_2CH_2CO_2H$ | $SCH_2CH_2CO_2H$ |
| 10 | H, 5-CH$_3$ | S | C≡C | H | $SCH_2CH_2CO_2H$ | $SCH_2CH_2C(O)N(CH_3)_2$ |
| 11 | H, 4-CH(CH$_3$)$_2$ | S | CH=CH | H | $SCH_2CH_2C(O)N(CH_3)_2$ | $SCH_2CH_2C(O)N(CH_3)_2$ |
| 12 | H, 4-CH(CH$_3$)$_2$ | S | CH=CH | H | $SCH_2CH_2CO_2H$ | $SCH_2CH_2C(O)N(CH_3)_2$ |

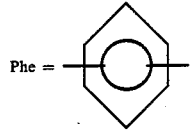

Compounds of the present invention can be prepared according to the following methods. Temperatures are in degrees Celsius.

METHOD A

Heterazole derivative III is transformed to adduct IV (where Z=a leaving group such as halogen) using a suitable reagent such as N-bromosuccinimide (NBS) in the presence of light. Halogen derivative IV is treated with Ph$_3$P in a solvent such as CH$_3$CN with heat, if necessary, to form Wittig reagent V.

Isophthaldehyde derivative of structure VI is reacted with an alkanoic acid or tetrazole substituted with a thiol or hydroxy group in an inert solvent such as benzene in the presence of a Suitable catalyst such as BF$_3$"OEt$_2$ or trimethylsilyl chloride to afford derivative VII.

Wittig reagent V is reacted with a base such as butyl lithium and the aldehyde VII to produce adduct VIII, a representative of structure I.

METHOD B

Compound IX is reacted with an alkanoic acid or tetrazole substituted with a thiol or hydroxy group in an inert solvent such as benzene in the presence of a suitable catalyst such as BF$_3$"OEt$_2$ or TMSCl to afford acetal derivative A. Acetal derivative X is then reacted with a derivative of general structure IV, in which Z is a leaving group such as a Br in the presence of a suitable base such as NaOH, NaH, or K₂CO₃ in an inert solvent such as THF, dioxane, DMF, etc, with warming, if necessary, to provide adduct XI, a representative of structure I.

METHOD C

Heterazole derivative III is treated with derivative VIa in the presence of a suitable catalyst like $ZnCl_2$ at a temperature above 120° or in hot acetic anhydride to give adduct XII. Bromoacid derivative XIII is treated first with 2 eq. of base such as BuLi in a suitable solvent such as THF at −100°, then at −78° with III to afford alcohol XIIIa. Alcohol XIIIa is reacted with thiol XIV in the presence of a suitable catalyst such as $BF_3$ or $AlCl_3$ to give adduct XV.

METHOD D

Alternatively, adduct XIIIa can be transformed to XVI where W is a suitable leaving group such as Cl using reaction conditions such as $CCl_4$/trioctylphosphine. XVI is reacted with thiol XIV in the presence of a suitable base such as $K_2CO_3$ to give adduct XV.

METHOD E

Referring to Method E, derivative IV is reacted with a compound of formula IX in the presence of a suitable base such as NaOH, NaH, $K_2CO_3$ or NaOMe in an inert solvent such as THF with warming, if necessary, to provide the adduct XIIa. Using the reactions described in Methods C or D adduct XIIa is transformed to XVII.

METHOD F

Referring to Method F, bromo derivative XVIII can be treated with $Ph_3P$ in a suitable solvent such as toluene or $CH_3CN$ with warming, if necessary, to provide phosphonium salt XIX. The phosphonium salt XIX is first treated with n-butyllithium then with lactol XX to afford styrene adduct XXI. Alcohol XXI is transformed to ester XXII using conventional methods such as $CrO_3$/pyridine followed by $MnO_2$/NaCN/AcOH. Styrene adduct XXII is condensed with thiol XIV is the presence of a suitable catalyst such as $AlCl_3$ to give thiol ether XXIII.

When A=CN, XXIII is converted to the aldehyde XXIV using a suitable reagent such as $SnCl_2$/HCl. The phosphonium salt V is first treated with n-butyl lithium then with XXIV to give heterazole XXV.

When A=OMe, XXIII is demethylated using a suitable reagent such as $BBr_3$ or $AlCl_3$/HSEt to give phenol derivative XXVI. Phenol XXVI is condensed with heterazole derivative IV using a suitable catalyst such as $K_2CO_3$ to afford adduct XXVII.

METHOD G

Referring to Method G, heterazole derivative III is first treated with LDA and then with bromo derivative XVIIIa to afford adduct XXVIII. Cyano derivative XXVIII is reduced to aldehyde XXIX with a reagent such as $SnCl_2$/HCl. Using the methodology described in Method C or D XXIX is converted to XXX.

METHOD H

Intermediate XII from Method C is treated with a mixture of two different thiols in the presence of a suitable catalyst such as boron trifluoride etherate ($BF_3''O$-$Et_2$) or trimethyl-silyl chloride (TMSCl). This generates a mixture of the three possible dithioacetals (or dithioketals) XXXI, XXXII and XXXIII, each of which is a representative of structure I.

The groups $Q^1$ and $Q^2$ may be modified by hydrolysis of an ester group, removal of a blocking group, or conversion of a nitrile to an amide or tetrazole by heating with tributyltin azide, thus providing additional examples of the leukotriene antagonists of the present invention.

In the following schema Az represents

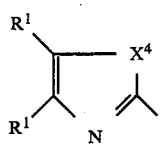

METHOD A

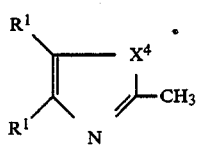

III

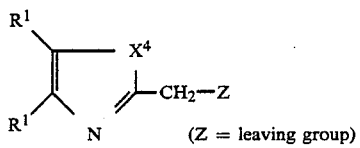

(Z = leaving group)

IV 4,962,117
-continued
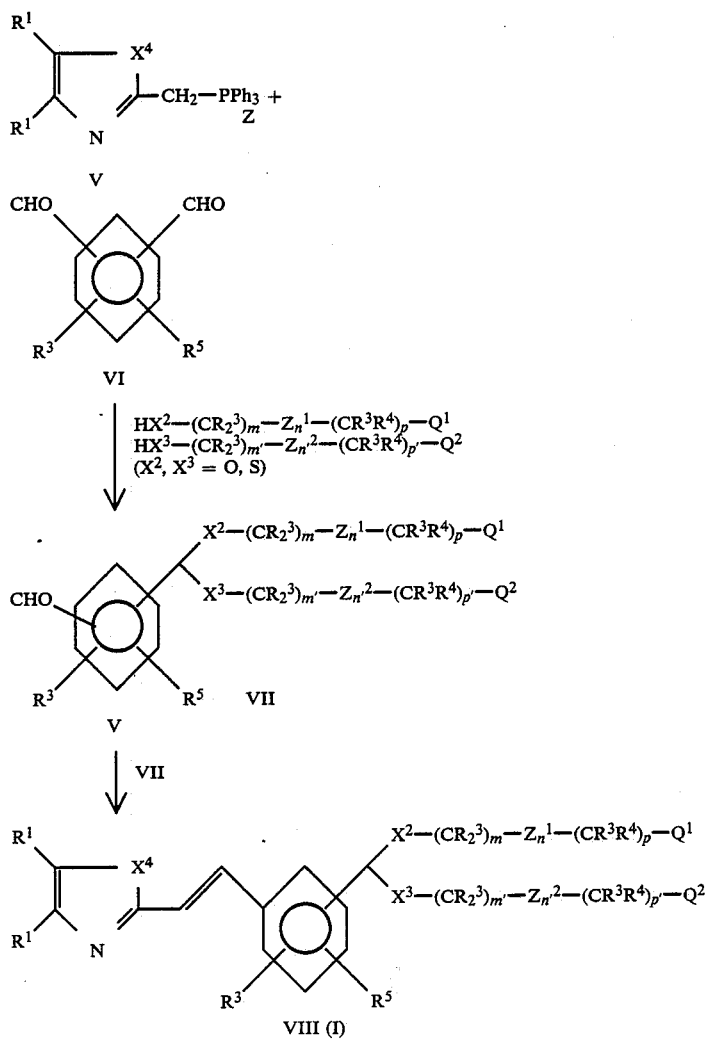
METHOD B
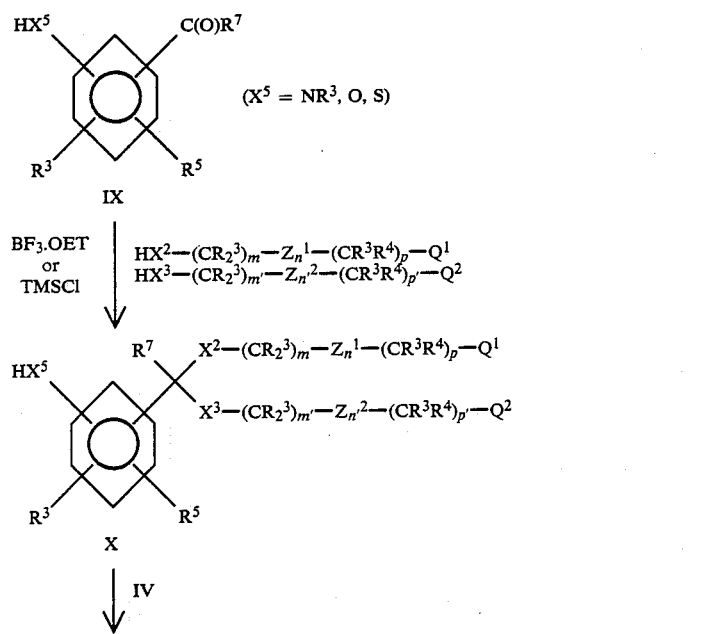

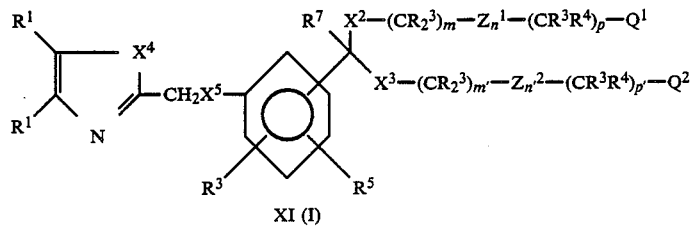
METHOD C
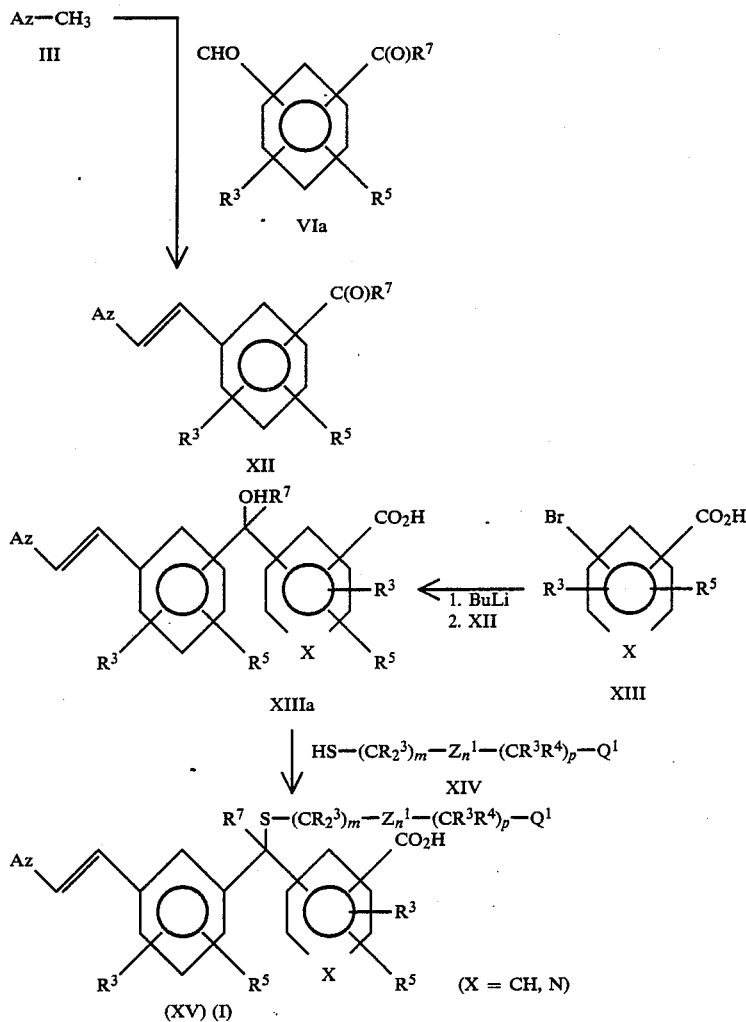
METHOD D
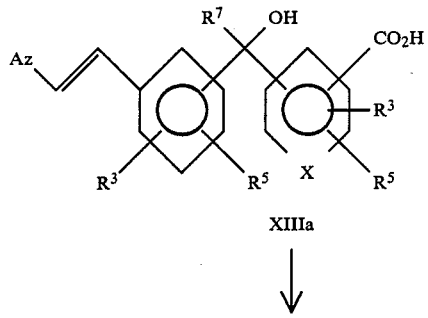

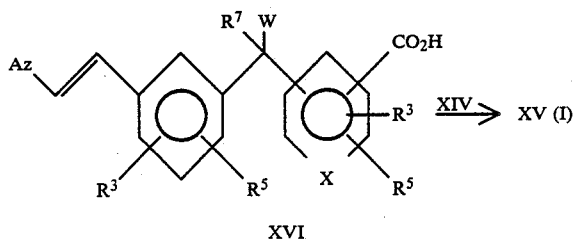
METHOD E
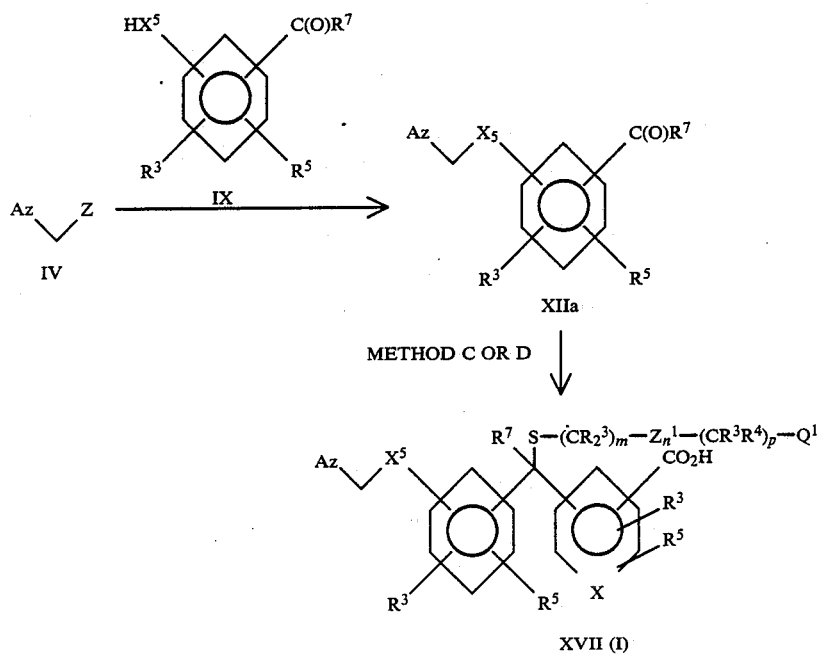
METHOD F
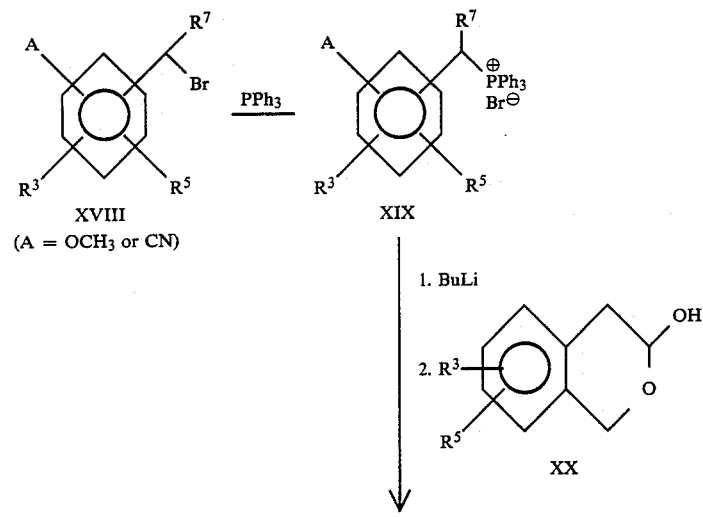

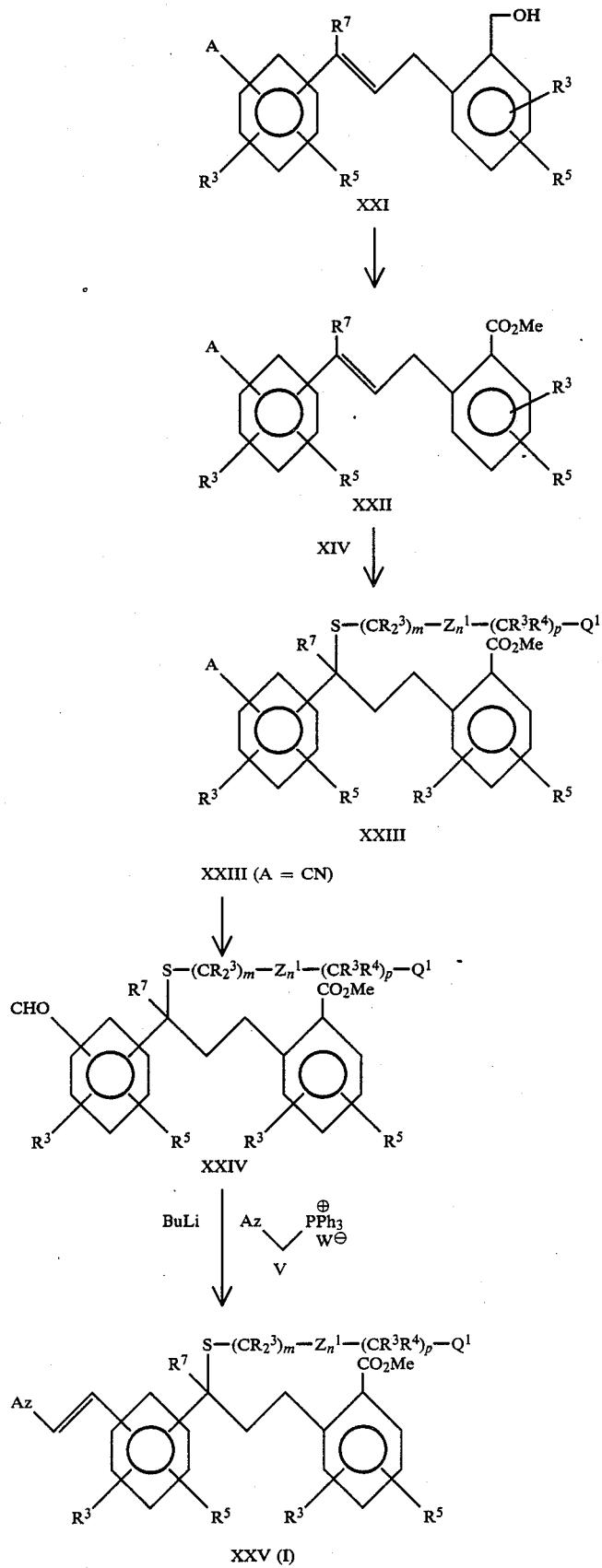

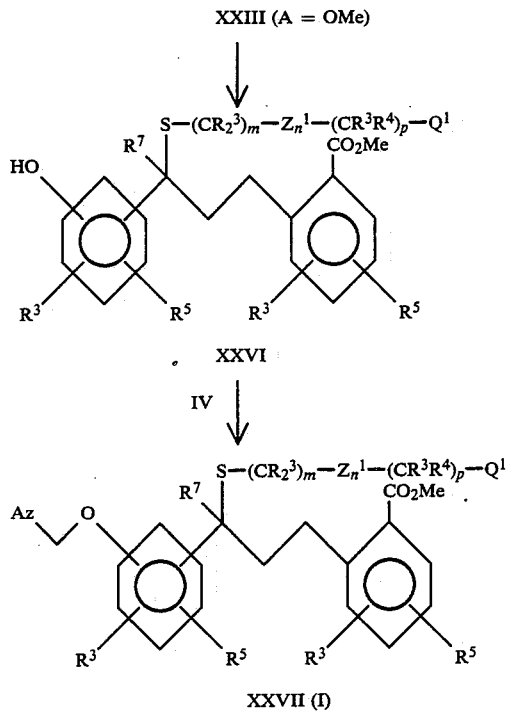
METHOD G
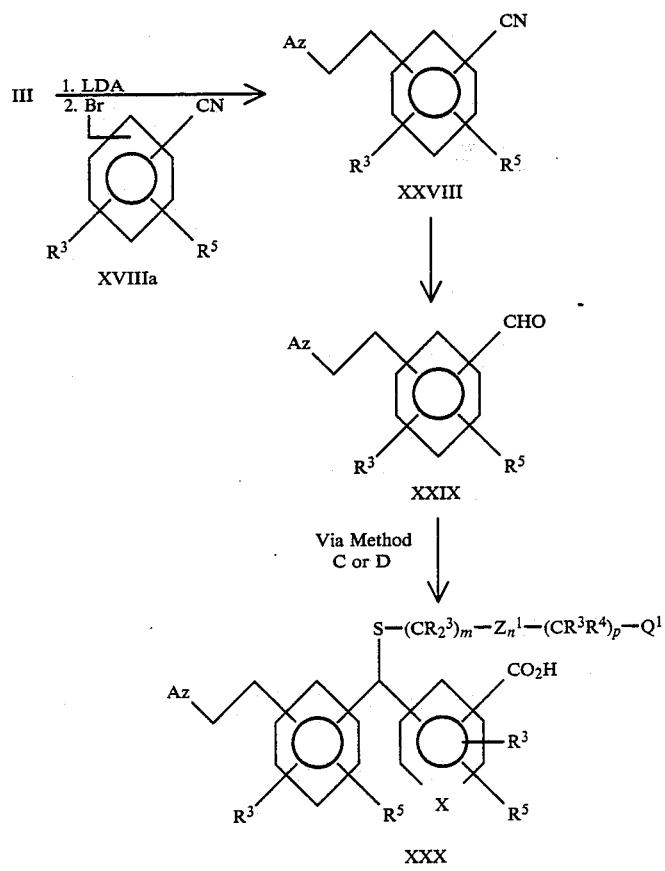
METHOD H

-continued

XII + HS—(CR$_2^3$)$_m$—Z$_n^1$—(CR$^3$R$^4$)$_p$—Q$^1$ + HS—(CR$_2^3$)$_{m'}$—Z$_{n'}^2$—(CR$^3$R$^4$)$_{p'}$—Q$^2$ $$\downarrow \text{BF}_3.\text{OEt}_2 \text{ or TMSCl}$$

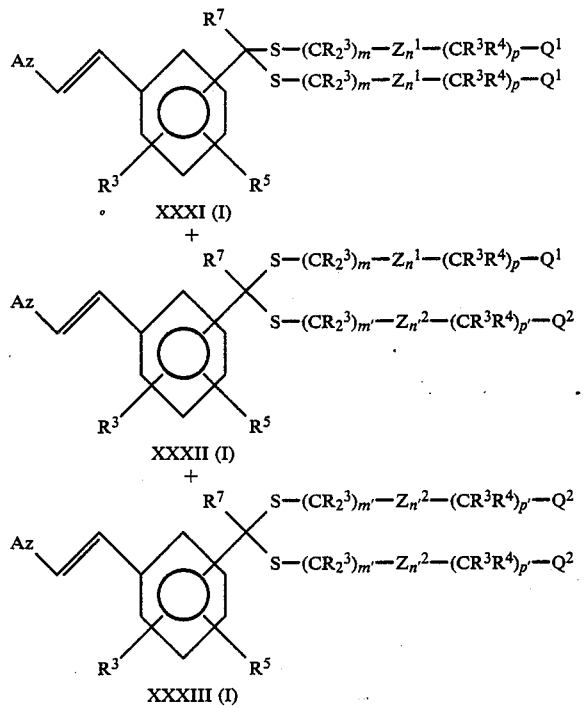

XXXI (I)
+
XXXII (I)
+
XXXIII (I)

EXAMPLE 2

3,3'-(((3 (2-(4-(1-Methylethyl)-2-thiazolyl)ethenyl)-phenyl)methylene)bis(thio)))bispropanoic acid Using the procedure of Example 12, but adding 2.5 equiv. (instead 1.2) of LiOH 1.0 N, dimethyl 3,3'-(((3-(2-(4-(1-methylethyl)-2-thiazolyl) -ethenyl)phenyl)methylene)bis(thio)))bispropanoate (192 mg, from Example 11, Step 2) is hydrolyzed to the title diacid.

$^1$H NMR (CDCl$_3$.DMSO)δ1.34 (d, 6H), 2.57 (t, 4H), 2.82 (m, 4H), 3.12 (m, 1H), 5.07 (s, 1H), 6.85 (s, 1H), 7.30–7.48 (m, 5H), 7.64 (s, 1H) ppm.

Anal. calc'd for C$_{23}$H$_{29}$N$_2$O$_3$S$_3$Na: C, 55.18; H, 5.84; N, 5.60; S, 19.21; Na, 4.59 Found: C, 55.05; H, 5.97; N, 5.44; S, 19.53; Na, 4.07.

EXAMPLE 11

N,N,N',N'-tetramethyl 3,3'-(((3-(2-(4-(1-methylethyl) -2-thiazolyl)ethenyl)phenyl)methylene)bis(thio))-bispropanamide

Step 1: Preparation of 3-(2-(4-(1-methylethyl)-2-thiazolyl)ethenyl)benzaldehyde 4-(1-Methylethyl)-2-methylthiazole (546 mg, EP 0219436 p. 19) and isophthaladehyde (570 mg, 1.1 equiv.) are heated at reflux in acetic anhydride (1.1 mL, 3 equiv.) 16 hours. The reaction mixture is cooled and the acetic acid and anhydride are co-evaporated with toluene. The title compound is purified by flash chromatography on silica using EtOAc:hexane 10:90.

$^1$H NMR (CHCl$_3$) δ1.35 (d, 6H), 3.12 (m, 1H), 6.87 (s, 1H), 7.33–7.49 (AB system, 2H), 7.55 (t, 1H), 7.78 (d, 1H), 7.83 (d, 1H), 8.02 (s, 1H), 10.04 (s, 1H) ppm.

Step 2:

To a solution of the aldehyde of Step 1 (430 mg), methyl 3-mercaptopropanoate (190 μL, 1 equiv.) and N,N-dimethyl 3-mercaptopropanamide (223 mg, 1 equiv.) in CH$_2$Cl$_2$ (10 mL), BF$_3$.Et$_2$O (620 μL, 3 equiv.) is added slowly and the mixture is stirred 1.5 hours. The reaction is quenched with 25% aqueous NH$_4$OAc at 0° C. The products are extracted with EtOAc and separated by flash chromatography on silica using a gradient of EtOAc:toluene (from 10:90 to 40:60) and acetone:toluene 1:1. Three products are obtained: first, dimethyl 3,3'(((3-(2-(4-(1-methylethyl)-2-thiazolyl)ethenyl)-phenyl)methylene)-bis (thio))bispropanoate; second, methyl 3-((1-((3-dimethylamino-3-oxopropyl)thio)-1-(3-(2-(4-( 1-methyl-ethyl)-2-thiazolyl)ethenyl)phenyl)methyl)thio)-propanoate; and third, the title compound.

$^1$H NMR (CDCl$_3$) δ1.35 (d, 6H), 2.56 (t, 4H), 2.82–2.97 (m, 16H), 3.12 (m, 1H), 5.08B (s, 1H), 6.82 (s, 1H), 7.2–7.47 (m, 5H), 7.67 (s, 1 H) ppm.

EXAMPLE 12

3-((1-((3-Dimethylamino-3-oxopropyl)thio)-1-(3-(2-(4-(1-methylethyl)-2-thiazolyl)ethyl)phenyl)methyl)thio)-propanoic acid At 0° C., LiOH 1.0 N (910 μL, 1.2 equiv.) is added to methyl 3-((1-((3-dimethylamino-3-oxopropyl)-thio)-1-(3-(2-(4-(1-methylethyl) -2-thiazolyl)ethenyl)-phenyl)-methyl)thio)propanoate (372 mg, from Example 11, Step 2) in THF (4 mL). The reaction mixture is stirred at 0° C. 6.5 hours, and 25% aqueous NH₄OAc is added, followed by AcOH (approx. 500 μL). The product is extracted with EtOAc, dried over Na₂SO₄, concentrated, stripped with toluene and purified by flash chromatography on silica using acetone:toluene:AcOH 15:85:1, 20:80:1, and 25:75:1.

¹H NMR (CDCl₃) δ1.35 (d, 6H), 2.62-3.2D (m, 15H), 5.10(s, 1H), 6.81 (s, 1H), 7 32-7 46 (m. 5H), 7.65 (s, 1H) ppm.

What is claimed is:

1. A compound of the formula:

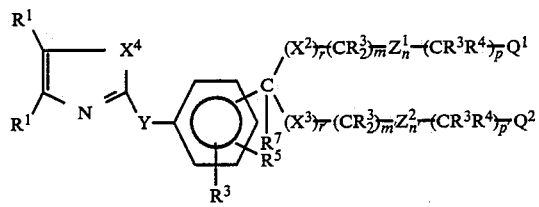

wherein:
- $R^1$ is H, halogen, $C_1$—$C_8$ alkyl, $C_2$—$C_8$ alkenyl, $C_2$—$C_8$ alkynyl, —$CF_3$, —$SR^2$, —$S(O)R^2$, —$S(O)_2R^2$, —$NR^3R^3$, —$OR^3$, —$COOR^3$, —(C=O)$R^3$, —$NR^3R^3$, —C(OH)$R^3R^3$, —CN, —$NO_2$, —$N_3$, substituted or unsubstituted phenyl, substituted or unsubstituted benzyl, substituted or unsubstituted 2-phenethyl, or substituted or unsubstituted pyridyl, (wherein substituted means 1 or 2 substituents on the aromatic ring selected from $C_1$—$C_6$ alkyl, $R^{10}$, $NO_2$, $SCF_3$, —$COR^7$, —$COR^{10}$, CN, halogen, and $CF_3$)
- $R^2$ is $C_1$—$C_8$ alkyl, $C_2$—$C_8$ alkenyl, $C_2$—$C_8$ alkynyl, —$CF_3$, substituted or unsubstituted phenyl, substituted or unsubstituted benzyl, or substituted or unsubstituted 2-phenethyl;
- $R_3$ is H or $R^2$;
- $R^4$ is H, halogen, —$NO_2$, —CN, —$OR^3$, —$SR^3$, $NR^3R^3$, or $C_1$—$C_8$ alkyl;
- $R^5$ is H, halogen, —$NO_2$, —$N_3$, —CN, —$SR^2$, —$NR^3R^3$, —$OR^3$, $C_1$—$C_8$ alkyl, or —(C=O)$R^3$;
- $R^6$ is —$(CH_2)_s$—$C(R^7R^7)$-$(CH_2)_s$—$R^8$ or —$CH_2CONR^{12}R^{12}$;
- $R^7$ is H or $C_1$—$C_4$ alkyl;
- $R^8$ is (A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or (B) the radical W-$R^9$;
- $R^9$ contains up to 21 carbon atoms and is (1) a hydrocarbon radical or (2) an acyl radical of an organic acyclic or monocyclic carboxylic acid containing not more than 1 heteroatom in the ring;
- $R^{10}$ is —$SR^{11}$, —$OR^{12}$, or —$NR^{12}R^{12}$;
- $R^{11}$ is $C_1$—$C_6$ alkyl, —(C=O)$R^{14}$, unsubstituted phenyl, or unsubstituted benzyl;
- $R^{12}$ is H, $R^{11}$, or two $R^{12}$ groups joined to the same N may form a ring of 5 or 6 members containing up to two heteroatoms chosen from O, S or N;
- $R^{13}$ is $C_1$—$C_8$ alkyl, $C_2$—$C_8$ alkenyl, $C_2$—$C_8$ alkynyl, —$CF_3$, or unsubstituted phenyl, benzyl, or 2-phenethyl;
- $R^{14}$ is H or $R^{13}$;
- $R^{15}$ is $R^3$ or halogen;
- $R^{16}$ is H, $C_1$—$C_4$ alkyl, or OH;
- m and m' are independently 0-8;
- n and n' are independently 0 or 1;
- p and p' are independently 0-8;
- m+n+p is 1-10 when $X^2$ is O, S, S(O), or S(O)₂;
- m+n+p is 0-10 when $X^2$ is $CR^3R^{16}$;
- m'+n'+p' is 1-10 when $X^3$ is O, S, S(O), or S(O)₂;
- m'+n'+p' is 0-10 when $X^3$ is $CR^3R^{16}$;
- r is O or 1 when $Z^1$ is HET (—$R^3$, —$R^5$);
- r is 1 when $Z^1$ is —$CONR^3$;
- r' is O or 1 when $Z^2$ is HET(—$R^3$, —$R^5$);
- r' is 1 when $Z^2$ is $CONR^3$;
- s is 0-3;
- $Q^1$ and $Q^2$ are independently —$COOR^3$, tetrazole, —$COOR^6$, —$CONHS(O)_2R^{13}$, —CN, —$CONR^{12}R^{12}$, —CHO, —$CH_2OH$, —$COCH_2OH$, —$NHS(O)_2R^{13}$; or if $Q^1$ or $Q^2$ is COOH and $R^4$ is —OH, —SH, or —$NHR^3$ then $Q^1$ or $Q^2$ and $R^4$ and the carbons through which they are attached may form a heterocyclic ring by loss of water;
- W is O, S, or $NR^3$;
- $X^1$ is O, S, —S(O)—, —$S(O)_2$—, —$NR^3$, or —$CR^3R^3$;
- $X^2$ and $X^3$ are independently O, S, S(O), S(O)₂, or $CR^3R^{16}$;
- $X^4$ is $NR^3$, O, or S;
- Y is —$CR^3$=$CR^3$—, —C≡C—, —$CR^3R^3$—$X^1$—, —$X^1$—$CR^3R^3$—, —$CR^3R^3$—$X^1$—$CR^3R^3$—,

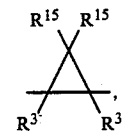

C=O,

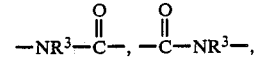

O, S, or $NR^3$;
- $Z^1$ and $Z^2$ are independently —$CONR^3$—or —HET(—$R^3$, —$R^5$)—;
- HET is

and the pharmaceutically acceptable salts thereof.

2. A compound of claim 1 of Formula I' wherein the substituents are as follows:

| $R^1, R^1$ | $X^4$ | Y | $R^5$ |
|---|---|---|---|
| H, H | S | CH=CH | H |
| H, 4-CH(CH₃)₂ | S | CH=CH | H |
| H, 5-CH(CH₃)₂ | S | CH=CH | H |
| H, 4-CH(CH₃)₂ | O | CH=CH | 6-CH₃ |
| H, 4-CH(CH₃)₂ | NCH₃ | CH=CH | H |
| CH₃, CH₃ | S | CH₂O | 4-Br |
| H, Cl | S | CH₂S | H |
| H, 5-CF₃ | S | CH=CH | H |
| H, 4-CH(CH₃)₂ | S | C≡C | H |
| H, 5-CH₃ | S | C≡C | H |
| H, 4-CH(CH₃)₂ | S | CH=CH | H |
| H, 4-CH(CH₃)₂ | S | CH=CH | H |

-continued

| R¹, R¹ | A | B |
|---|---|---|
| H, H | SCH₂CH₂CO₂H | SCH₂CH₂CO₂H |
| H, 4-CH(CH₃)₂ | SCH₂CH₂CO₂H | SCH₂CH₂CO₂H |
| H, 5-CH(CH₃)₂ | SCH₂CH₂CO₂H | SCH₂CH₂CO₂H |
| H, 4-CH(CH₃)₂ | SCH₂CH₂CO₂H | SCH₂CH₂C(O)N(CH₃)₂ |
| H, 4-CH(CH₃)₂ | SCH₂CH₂CO₂H | SCH₂CH₂CO₂H |
| CH₃, CH₃ | SCH₂CH₂CO₂H | 3-(CO₂H)Phe |
| H, Cl | SCH₂CH₂C(O)N(CH₃)₂ | CH₂CH₂-2-(CO₂H)Phe |
| H, 5-CF₃ | SCH₂CH₂CO₂H | 2-(CO₂H)—Phe |
| H, 4-CH(CH₃)₂ | SCH₂CH₂CO₂H | SCH₂CH₂CO₂H |
| H, 5-CH₃ | SCH₂CH₂CO₂H | SCH₂CH₂C(O)N(CH₃)₂ |
| H, 4-CH(CH₃)₂ | SCH₂CH₂C(O)N(CH₃)₂ | SCH₂CH₂C(O)N(CH₃)₂ |
| H, 4-CH(CH₃)₂ | SCH₂CH₂CO₂H | SCH₂CH₂C(O)N(CH₃)₂ |

3. A compound of claim 1 wherein:
$R^1$ is H, halogen, $C_1$—$C_8$ alkyl, —$CF_3$, —$SR^2$, —S(O)$R^2$, —$S(O)_2R^2$, —$OR^3$, or —CN;
$R^2$ is $C_1$—$C_8$ alkyl or —$CF_3$;
$R^3$ is H or $R^2$;
$R^4$ is H, —$OR^3$, —$SR^3$, $NR^3R^3$, or $C_1$—$C_8$ alkyl;
$R^5$ is H, halogen, —CN, —$SR^2$, —$OR^3$, $C_1$–$C_8$ alkyl, or —(C=O)$R^3$;
$R_6$ is —(CH$_2$)$_s$—C($R^7R^7$)—(CH$_2$)$_s$—$R^8$ or —CH$_2$CONR$^{12}$R$^{12}$;
$R_7$ is H or $C_1$—$C_4$ alkyl;
$R^8$ is (A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or (B) the radical W-$R^9$;
$R^9$ contains up to 21 carbon atoms and is (1) a hydrocarbon radical or (2) an acyl radical of an organic acyclic or monocyclic carboxylic acid containing not more than 1 heteroatom in the ring;
$R^{10}$ is —$SR^{11}$, —$OR^{12}$, or —$NR^{12}R^{12}$;
$R^{11}$ is $C_1$—$C_6$ alkyl, —(C=O)$R^{14}$, unsubstituted phenyl, or unsubstituted benzyl;
$R^{12}$ is H, $R^{11}$, or two $R^{12}$ groups joined to the same N may form a ring of 5 or 6 members containing up to two heteroatoms chosen from O, S or N;
$R^{13}$ is $C_1$—$C_8$ alkyl, —$CF_3$, or unsubstituted phenyl, benzyl, or 2-phenethyl;
$R^{14}$ is H or $R^{13}$;
$R^{15}$ is $R^3$ or halogen;
$R^{16}$ is H, $C_1$—$C_4$ alkyl, or OH;
m and m' are independently 0–4;
n and n' are independently 0 or 1;
p and p' are independently 0–4;
m+n+p is 1–10 when $X^2$ is O or S;
m+n+p is 0–10 when $X^2$ is $CR^3R^{16}$;
m'+n'+p' is 1–10 when $X^3$ is O or S;
m'+n'+p' is 0–10 when $X^3$ is $CR^3R^{16}$;
r is 0 or 1 when $Z^1$ is HET (—$R^3$, —$R^5$);
r is 1 when $Z^1$ is —$CONR^3$;
r' is 0 or 1 when $Z^2$ is HET(—$R^3$,—$R^5$);
r' is 1 when $Z^2$ is $CONR^3$;
s is 0–3;

$Q^1$ and $Q^2$ are independently —$COOR^3$, tetrazole, —$COOR^6$, —$CONHS(O)_2R^{13}$, —$CONR^{12}R^{12}$, —$NHS(O)_2R^{13}$; or if $Q^1$ or $Q^2$ is COOH and $R^4$ is —OH, —SH, or —$HNR^3$ then $Q^1$ or $Q^2$ and $R^4$ and the carbons through which they are attached may form a heterocyclic ring by loss of water;
W is O, S, or NH;
$X^1$ is O, S, —$NR^3$, or —$CR^3R^3$—;
$X^2$ and $X^3$ are independently O, S, or $CR^3R^{16}$;
$X^4$ is $NR^3$, O, or S;
Y is —$CR^3$=$CR^3$—, —C≡C—, —$CR^3R^3$13 $X^1$—, or —$X^1$—$CR^3R^3$—;
$Z^1$ and $Z^2$ are independently —$CONR^3$— or —HET-(—$R^3$,—$R^5$)—;
HET is

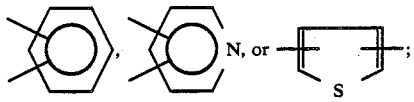

and the pharmaceutically acceptable salts thereof.

4. A pharmaceutical composition for antagonizing leukotrienes comprising a therapeutically effective amount of a compound of claim 1 and a pharmaceutically acceptable carrier.

5. The pharmaceutical composition of claim 4 additionally comprising an effective amount of a second active ingredient selected from the group consisting of non-steroidal anti-inflammatory drugs; peripheral analgesic agents; cyclooxygenase inhibitors; leukotriene antagonists; leukotriene bisynthesis inhibitors; H₂-receptor antagonists; antihistaminic agents; prostaglandin antagonists; thromboxane antagonists; thromboxane synthetase inhibitors; and ACE antagonists.

6. A pharmaceutical composition according to claim 5, wherein the second active ingredient is a non-steroidal anti-inflammatory drug.

7. A pharmaceutical composition of claim 6, wherein the weight ratio of said compound of claim 1 to said second active ingredient ranges from about 1000:1 to 1:1000.

8. A method of preventing the synthesis, the action, or the release of SRS-A or leukotrienes in a mammal which comprises administering to said mammal an effective amount of a compound of claim 1.

9. The method of claim 8 wherein the mammal is man.

10. A method of inducing cytoprotection in a mammal comprising administering to a mammal in need of such treatment a cytoprotective amount of a compound of claim 1.

11. A method of treating inflammatory diseases of the eye in a mammal which comprises administering to a mammal in need of such treatment a therapeutically effective amount of a compound of claim 1.

12. The method of claim 11 wherein the mammal is man.

* * * * *